US010966663B2

(12) United States Patent
Lorato

(10) Patent No.: US 10,966,663 B2
(45) Date of Patent: Apr. 6, 2021

(54) METHOD AND A SYSTEM FOR DETECTING A VITAL SIGN OF A SUBJECT

(71) Applicant: STICHTING IMEC NEDERLAND, Eindhoven (NL)

(72) Inventor: Ilde Rosa Lorato, Leuven (BE)

(73) Assignee: STICHTING IMEC NEDERLAND, Eindhoven (NL)

( * ) Notice: Subject to any disclaimer, the term of this patent is extended or adjusted under 35 U.S.C. 154(b) by 316 days.

(21) Appl. No.: 16/023,352

(22) Filed: Jun. 29, 2018

(65) Prior Publication Data

US 2019/0008459 A1      Jan. 10, 2019

(30) Foreign Application Priority Data

Jul. 5, 2017   (EP) .................................... 17179742

(51) Int. Cl.
| | | |
|---|---|---|
| *A61B 5/00* | (2006.01) | |
| *A61B 5/024* | (2006.01) | |
| *A61B 5/05* | (2021.01) | |
| *A61B 5/08* | (2006.01) | |
| *G01S 7/35* | (2006.01) | |

(Continued)

(52) U.S. Cl.
CPC ............ *A61B 5/7214* (2013.01); *A61B 5/024* (2013.01); *A61B 5/05* (2013.01); *A61B 5/0816* (2013.01); *A61B 5/726* (2013.01); *A61B 5/7207* (2013.01); *A61B 5/7235* (2013.01); *A61B 5/7278* (2013.01); *G01S 7/354* (2013.01);

(Continued)

(58) Field of Classification Search
None
See application file for complete search history.

(56) References Cited

U.S. PATENT DOCUMENTS

| | | | | |
|---|---|---|---|---|
| 2010/0130873 | A1* | 5/2010 | Yuen ..................... | A61B 5/0507 600/484 |
| 2010/0198083 | A1* | 8/2010 | Lin ....................... | A61B 5/6823 600/484 |
| 2015/0164375 | A1* | 6/2015 | Schindhelm .......... | A61B 5/7221 600/534 |

FOREIGN PATENT DOCUMENTS

WO    WO-2016046789 A1    3/2016

OTHER PUBLICATIONS

Petrochilos et al., "Blind Separation of Human Heartbeats and Breathing by the Use of a Doppler Radar Remote Sensing", IEEE International Conference on Acoustics, Speech and Signal Processing—ICASSP '07, pp. I-333-I-336, 2007.

(Continued)

*Primary Examiner* — Katherine L Fernandez
(74) *Attorney, Agent, or Firm* — Moser Taboada

(57) ABSTRACT

A method for detecting a vital sign of a subject (102) comprises: receiving (302) a reflected radio frequency signal from the subject (102), the reflected signal being based on a transmitted signal, which is Doppler-shifted due to mechanical movements corresponding to the heart rate and/or the respiratory rate; dividing (304) a baseband signal into a sequence of sliding windows (200), each sliding window (200) representing a time interval; estimating (306) a vital sign parameter in at least one sliding window (200); determining (308) whether a vital sign parameter may be reliably estimated in at least one sliding window (200); on condition that the vital sign parameter may not be reliably estimated in a sliding window (200), determining (310) a vital sign parameter of the sliding window (200) based on vital sign parameters estimated in a plurality of windows representing time intervals close to the time interval of the window (200).

15 Claims, 4 Drawing Sheets

(51) Int. Cl.
  G01S 13/50      (2006.01)
  A61B 5/113      (2006.01)
(52) U.S. Cl.
  CPC ............... *G01S 13/50* (2013.01); *A61B 5/113* (2013.01); *A61B 5/7264* (2013.01); *G01S 2007/358* (2013.01)

(56) References Cited

OTHER PUBLICATIONS

Li et al., "Random Body Movement Cancellation in Doppler Radar Vital Sign Detection", IEEE Transactions on Microwave Theory and Techniques, vol. 56, Issue 12, pp. 3143-3152, Dec. 2008.

Morgan et al., "Novel Signal Processing Techniques for Doppler Radar Cardiopulmonary Sensing", Signal Processing, vol. 89, Issue 1, pp. 45-66, Jan. 2009.

Fletcher et al., "Low-Cost Differential Front-End for Doppler Radar Vital Sign Monitoring", IEEE MTT-S International Microwave Symposium Digest, pp. 1325-1328, Jun. 2009.

Mijovic et al., "Source Separation from Single-Channel Recordings by Combining Empirical-Mode Decomposition and Independent Component Analysis", IEEE Transactions on Biomedical Engineering, vol. 57, Issue 9, pp. 2188-2196, Sep. 2010.

Zakrzewski et al., "Separating Respiration Artifact in Microwave Doppler Radar Heart Monitoring by Independent Component Analysis", IEEE Sensors Conference, pp. 1368-1371, Nov. 2010.

Mostafanezhad et al., "Cancellation of Unwanted Doppler Radar Sensor Motion Using Empirical Mode Decomposition", IEEE Sensors Journal, vol. 13, Issue 5, pp. 1897-1904, May 2013.

Zakrzewski., "Methods for Doppler Radar Monitoring of Physiological Signals", Phd Thesis, Tampere University of Technology, 2015.

Kagawa et al., "Sleep Stage Classification by Non-Contact Vital Signs Indices Using Doppler Radar Sensors", 38th Annual International Conference of the IEEE Engineering in Medicine and Biology Society, pp. 4913-4916, Aug. 16, 2016.

Extended European Search Report dated Jan. 3, 2018 for Application No. EP17179742.6.

\* cited by examiner

METHOD AND A SYSTEM FOR DETECTING A VITAL SIGN OF A SUBJECT

CROSS-REFERENCE TO RELATED APPLICATIONS

This application claims priority to and the benefit of European Patent Application No. 17179742.6, filed on Jul. 5, 2017, the disclosure of which is incorporated herein by reference in its entirety.

TECHNICAL FIELD

The present inventive concept relates to a method and a system for detecting a vital sign of a subject. In particular, the present inventive concept relates to radar-based technique for detecting a vital sign of a subject, including transmitting a radio frequency waveform and receiving a reflected waveform.

BACKGROUND

In recent year, contactless health monitoring has become an increasingly hot topic. For that reason, radar techniques are of high interest as it offers contactless monitoring. Radar techniques have been investigated for vital signs monitoring, such as determining a heartbeat rate and/or a respiratory rate of a subject.

The radar techniques may utilize a Doppler shift that is caused by mechanical movements of heart and chest (lungs) in order to detect the mechanical movements which may be converted to measurements of the heartbeat rate and respiratory rate.

The limit of current devices is that it is possible to monitor heartbeat and respiration rate under "ideal condition", that is, with subjects constrained to be motionless (i.e., seated or lying down avoiding any kind of random body movement). In fact, the received signals may be strongly disturbed by the influence of random body movements, such as movements of arms and legs or other parts of the body. The random body movements may be at least an order of magnitude larger than the pulmonary activity (typical frequency is within 0.1-0.3 Hz and the amplitude is about 10 mm) and the heart movement (typical frequency is within 1-1.5 Hz and the amplitude is about 0.1 mm).

Some solutions have been proposed for solving the problem of random body movements destroying possibilities of determining vital signs. For instance, in US 2010/0198083, a method for cancelling body movement effect for non-contact vital sign detection is described. The method comprises sending a first electromagnetic signal to a first side of a body and sending a second electromagnetic signal to a second side of a body, wherein the first and second electromagnetic signals have different frequencies. Based on first and second reflected electromagnetic signals, first and second baseband complex signals are extracted. The first baseband complex signal is mathematically combined with the second baseband complex signal to cancel out a Doppler frequency drift therebetween to yield a periodic Doppler phase effect.

However, the method is based on a human subject being perfectly positioned in between two radars, positioned respectively in front and on the back of the human subject. Further, the method is based on the random movements producing two baseband signals with the same amplitude but out-of-the-phase, while the periodic vital signs movements produce two identical signals. Adding the two baseband signals, the resulting single channel signal will contain only the desired information. As it can be easily understood, this method still applies to random body movements occurring in ideal conditions. In fact, (1) the body random movements have to be within few millimeters, (2) the subject has to be perfectly in between the two radars, (3) the radars should perform exactly the same without any unbalance, and (4) the vital signs displacements are the same from the front and the back.

Thus, there still remains a need of decreasing sensitivity of vital signs detection to random body movements.

SUMMARY

It is an object of the present inventive concept to improve random body movement rejection in vital signs detection. It is another object of the present inventive concept to enable vital signs detection without severely constraining the subject so as to enable vital signs detection in a real-life situation.

These and other objects of the present inventive concept are at least partly met by the invention as defined in the independent claims. Preferred embodiments are set out in the dependent claims.

According to a first aspect, there is provided a method for detecting a vital sign of a subject, comprising at least one of a heart rate and a respiratory rate of the subject, said method comprising: receiving a reflected radio frequency signal from the subject, the reflected signal being based on a transmitted signal, which is Doppler-shifted due to mechanical movements corresponding to at least one of the heart rate and the respiratory rate to form the reflected signal; dividing a baseband signal based on the received signal and the transmitted signal into a sequence of sliding windows, wherein each sliding window represents a time interval of the baseband signal; estimating a vital sign parameter based on the signal in at least one sliding window of the sequence of sliding windows; determining whether a vital sign parameter may be reliably estimated based on the signal in at least one sliding window of the sequence of sliding windows; on condition that the vital sign parameter may not be reliably estimated in a sliding window, determining a vital sign parameter of the sliding window based on vital sign parameters estimated in a plurality of windows representing time intervals close to the time interval of the window for which the vital sign parameter is determined.

The method enables detecting vital signs of a subject without requiring the subject to be completely motionless (or static) during acquiring of a signal for detecting vital signs. Thus, a subject may be quasi-static, performing random body movements intermittently during detection of vital signs. This provides a comfortable experience for the subject when examination of vital signs is performed. Also, vital signs may be determined in a real-life situation, e.g. determining vital signs of a subject that is sitting or lying in bed. For instance, the vital signs determination may function well in contactless monitoring of subjects in elderly care or monitoring of subjects while seated in a car, such as for monitoring a health condition of a driver.

The use of sliding windows may allow random body movements to be extracted so as to not disturb the determination of vital signs. As a random body movement occurs, the random body movement will only affect the estimation of vital signs in the sliding window(s) in which the random body movement occurs and not affect the entire acquired signal.

Further, by determining a vital sign parameter for the sliding window for which the signal does not allow the vital sign parameter to be reliably estimated, the sliding window in which a random body movement will not be completely ignored. On the contrary, the vital sign parameter is determined in the sliding window based on vital sign parameters estimated in adjacent sliding windows, which allows the sliding window to contribute to an overall determination of the vital sign parameter. Hence, the vital sign parameter may be more reliably determined as the vital sign parameter may be based on large amounts of data.

Since vital sign parameters may not change very quickly, determining a vital sign parameter for a sliding window based on sliding windows representing time intervals close to the sliding window may still provide a reliable value of the vital sign parameter in the sliding window.

The vital sign parameter that is estimated for a single sliding window may be output as a measure of the vital sign parameter in the time interval represented by the sliding window. Hence, updated measures of the vital sign parameter may be output for every sliding window allowing the method to continuously provide measures of the vital sign parameter. Further, there is no interruption in providing the vital sign parameter due to a random body movement occurring.

However, in other embodiments, a vital sign parameter may be determined as an average of the vital sign parameters estimated in each of the sliding windows. Hence, the vital sign parameter may not be output until a time period corresponding to a plurality of sliding windows has been acquired, and a single average for the time period may be determined. In this case, the vital sign parameters determined for the sliding windows in which random body movement occurred may still contribute to determining an overall average based on more data points. The vital sign parameter may be updated with every new set of data corresponding to a new sliding window, as the new set of data may be combined with previously acquired data for updating the average of the vital sign parameter being output.

The method may be implemented in real-time or near real-time so as to process data while being acquired and output measures of vital sign parameters in real-time or with a small delay. A small delay may be used in order to enable considering of sliding windows both before and after a sliding window in which a random body movement occurs, when determining the vital sign parameter for the sliding window in which the random body movement occurs.

The method may alternatively be implemented in a scenario where acquiring of signals from the subject occurs separated in time from processing of the signals. Thus, processing may occur at another time, e.g. for analysis of vital sign parameters in a population or other types of analysis that does not require real-time results.

The determining whether an estimated vital sign parameter may be reliably estimated in a sliding window may be based on analysis of a signal quality for the sliding window. Thus, it may be determined that a signal quality is so poor that it will not be possible to calculate a reliable estimate for the sliding window. Alternatively, if an estimate for a sliding window does not yield a plausible result, such fact may be used for determining that a vital sign parameter may not be reliably estimated. Hence, the estimating of vital sign parameters may be performed for each sliding window. However, the estimating of vital sign parameters need not necessarily be performed for each sliding window, but rather may be performed only for sliding windows determined to have sufficient signal quality (or not having insufficient signal quality).

The method according to claim 1, wherein two adjacent sliding windows in the sequence of sliding windows represent partially overlapping time intervals. Thanks to using partially overlapping time intervals in the sequence of sliding windows, it may be possible to use signals unaffected by random body movements to a very high degree, while still a time interval of the sliding window being relatively long (allowing determining of vital sign parameters with high accuracy). The use of partially overlapping time intervals implies that there is a high likelihood that a sliding window will end immediately before start of a random body movement, and also that there is a high likelihood that a sliding window will start immediately after end of the random body movement.

According to an embodiment, said determining whether an estimated vital sign parameter may be reliably estimated based on the signal in at least one sliding window of the sequence of sliding windows comprises comparing the estimated vital sign parameters of pairs of adjacent windows and determining whether a difference in the estimated vital sign parameters is above a threshold. Thus, vital sign parameters may be estimated for every sliding window. If a random body movement occurs within a sliding window, the vital sign parameter may be highly distorted for that sliding window, rendering an abnormal result. The distortion by the random body movement may thus be identified by means of the estimated vital sign parameters in adjacent sliding windows differing substantially. It should also be noted that a vital sign parameter, such as heartbeat rate or respiratory rate, may not normally change very quickly so it should be expected that the vital sign parameter for adjacent sliding windows is very similar.

Artefacts due to random body movements may be identified in other manners. Hence, according to other embodiments, said determining whether an estimated vital sign parameter may be reliably estimated based on the signal in at least one sliding window of the sequence of sliding windows comprises identifying an artefact in the signal in a sliding window. The identifying of the artefact may for instance be based on a continuous wavelet transform (CWT) or short-time Fourier transform (STFT) of the baseband signal, which transform may be formed based on a time period of the baseband signal extending over a plurality of sliding windows (and may be formed before dividing the baseband signal into sliding windows). The identifying of the artefact may also be performed after processing of the signal, e.g. filtering and/or smoothing, in order to try to cancel influence of a random body movement. Hence, the determination that a vital sign parameter may not be reliably estimated may be based on a signal that has been processed in an effort to enable estimation of the vital sign parameter despite occurrence of a random body movement.

It should be realized that many types of transforms and/or other processing operations may be performed on the baseband signal in order to determine signal quality and/or attenuate influence of random body movements.

According to an embodiment, the method further comprises at least partially cleaning the baseband signal to attenuate influence of artefacts. Thus, the baseband signal may be processed in order to be cleaned so as to remove artefacts. It may not be possible to completely remove artefacts, so the baseband signal may at least be partially cleaned in order to at least attenuate influence of artefacts.

The cleaning of the baseband signal may be performed prior to dividing the baseband signal into a sequence of sliding windows. However, in a real-time application, new data may be continuously received and sliding windows may be continuously defined and it may thus not be possible to perform processing on the entire baseband signal before it is divided into a sequence of sliding windows and estimation of vital sign parameters is initiated.

The cleaning of the baseband signal may be used in an effort to attenuate artefacts to such an extent that the baseband signal may still be used in sliding windows corresponding to the artefacts in order to reliably estimate vital sign parameter. Whether a vital sign parameter may in fact be reliably estimated may be determined e.g. based on comparing the estimated vital sign parameter in a sliding window after the cleaning of the baseband signal to the estimated vital sign parameter in an adjacent sliding window.

According to an embodiment, at least partially cleaning the baseband signal comprises determining time instances in the baseband signal in which an artefact is present. Determining time instances in which artefacts are present may enable applying cleaning operations to only the time instances in which artefacts are present.

According to an embodiment, determining time instances in the baseband signal in which an artefact is present comprises analyzing the baseband signal to determine time instances in which undesired high frequency components are present. As vital sign parameters are based on relatively slow frequencies (heartbeat rates are typically below 3 Hz), high frequency components will relate to distortions, e.g. caused by random body movements. Thus, by analyzing the baseband signal to find high frequency components may effectively be used in identifying artefacts.

The undesired high frequency components may be any frequency component that is higher than a bandwidth of normal vital signs. The undesired high frequency components may thus, for instance, be any frequency component having a frequency higher than 3 Hz.

According to an embodiment, at least partially cleaning the baseband signal further comprises applying a moving average filter to the signal in the determined time instances in which an artefact is present. Thus, an effect of the artefact may be attenuated based on signals around the artefact.

A moving average filter may be effectively used in an off-line process or a near real-time process, wherein the processing of a signal is not performed immediately upon acquiring of the signal.

In a real-time application, determining that an artefact is present in the baseband signal currently being acquired may trigger applying a filter to remove artefacts, such as a lowpass filter.

According to an embodiment, the baseband signal is acquired as an In-phase and a Quadrature (IQ) signal. The method may then comprise separately locating artefacts in the two channels of the IQ signal.

The two channels of the IQ signal may be combined, e.g. using linear demodulation, before a vital sign parameter is estimated based on the baseband signal in a sliding window.

According to an embodiment, estimating a vital sign parameter comprises converting the signal in the window to frequency domain and determining an estimated heart rate or respiratory rate based on a frequency of a peak in a frequency domain spectrum. If the vital sign parameter to be estimated is a heartbeat rate or a respiratory rate, it may be easily identified using analysis in frequency domain. The conversion of the signal to frequency domain may be performed e.g. using a fast Fourier transform (FFT).

According to an embodiment, estimating a vital sign parameter comprises detecting peaks in the signal in the window and determining an estimated heart rate or respiratory rate based on distance between adjacent peaks. For instance, an average time period between peaks may be used for determining an estimated heartbeat rate or respiratory rate. This implies that analysis of vital sign parameters may be performed in time domain and thus, that a transform operation for converting the signal to frequency domain may not be necessary.

According to an embodiment, determining an estimated heart rate or respiratory rate comprises ignoring rates which are outside a range of physiologically plausible rates. A signal may comprise several different intermixed frequency components or time periods between peaks and a vital sign parameter may be determined based on ignoring implausible rates.

According to an embodiment, the method further comprises receiving a window size setting and using the window size setting for defining a length of the time interval of each sliding window when dividing the baseband signal into a sequence of sliding windows.

Thus, a window size setting may be dynamically defined for a method of detecting a vital sign of a subject. This implies that the method may be adapted to external conditions or to signals received from a specific subject.

For instance, an initial analysis of the baseband signal may first be performed in order to determine a window size to be used. The initial analysis may include using a first default value of the window size and determining whether it would be beneficial to change the window size setting. Also, for an off-line process or a near real-time process, plural (at least two) determinations of vital sign parameters may be made using different window sizes on the same baseband signal, which may allow determination of a most plausible value of the vital sign parameter based on the different window sizes.

According to an embodiment, a length of the time interval of each sliding window is set in a range of 10-25 s. A long window implies that there is a larger risk that artefacts are present in a sliding window. On the other hand, a short window implies that it is difficult to precisely determine the vital sign parameters for an individual window, at least when a frequency domain approach is used for determining an estimated heart rate or respiratory rate in the individual window. Hence, a size of the sliding window in the range of 10-25 s may provide good results taking the above factors into consideration. However, different ranges may be used depending on e.g. how often random body movements or other artefacts occur.

According to an embodiment, the method further comprises splitting the baseband signal into a respiration information carrying signal and a heartbeat information carrying signal, performing estimation of respiration rate based on the respiration information carrying signal, and performing estimation of heart rate based on the heartbeat information carrying signal.

Thus, the baseband signal may be split such that contributions from the heartbeat rate and the respiration rate are separated, which may facilitate determination of each of the rates. The splitting may be based on knowledge of expected frequencies of each of the rates, such that e.g. a digital filter may be used in order to separate respiration information from heartbeat information.

According to an embodiment, a component analysis of the baseband signal is performed in order to split the baseband signal into the respiration information carrying signal and the heartbeat information carrying signal. For instance, a wavelet decomposition of the baseband signal may be performed.

According to an embodiment, said splitting of the baseband signal comprises performing wavelet decomposition of the baseband signal and using components produced by the wavelet decomposition as input to an independent component analysis for splitting the signal. An independent component analysis (ICA) method may only be able to separate independent signals if a number of observations is greater than or equal to a number of sources of the signals. Thus, when using a single radar, ICA may not be used for separating heartbeat information from respiratory information. However, in combination with wavelet decomposition, it is possible to successfully split the baseband signal into the respiration information carrying signal and the heartbeat information carrying signal.

According to an embodiment, said splitting of the baseband signal comprises decomposing the baseband signal into intrinsic mode functions using an ensemble empirical mode decomposition (EEMD) algorithm and using the intrinsic mode functions as input to an independent component analysis for splitting the signal. Using an EEMD algorithm in combination with ICA is another possibility of successfully splitting the baseband signal based on a single radar into the respiration information carrying signal and the heartbeat information carrying signal.

According to a second aspect, there is provided a device for detecting a vital sign of a subject, comprising at least one of a heart rate and a respiratory rate of the subject, said device comprising: a receiver, configured to detect a reflected radio frequency signal from the subject, the reflected signal being based on a transmitted signal, which is Doppler-shifted due to mechanical movements corresponding to at least one of the heart rate and the respiratory rate to form the reflected signal; a processor, which is configured to receive a baseband signal based on the detected signal from the receiver and the transmitted signal and which is further configured to: divide the baseband signal into a sequence of sliding windows, wherein each sliding window represents a time interval of the baseband signal; estimate a vital sign parameter based on the signal in at least one sliding window of the sequence of sliding windows; determine whether a vital sign parameter may be reliably estimated based on the signal in at least one sliding window of the sequence of sliding windows; on condition that the vital sign parameter may not be reliably estimated in a sliding window, determine a vital sign parameter of the sliding window based on vital sign parameters estimated in a plurality of windows representing time intervals close to the time interval of the window for which the vital sign parameter is determined.

Effects and features of this second aspect are largely analogous to those described above in connection with the first aspect. Embodiments mentioned in relation to the first aspect are largely compatible with the second aspect.

The system thus may be set up for monitoring an environment such that detecting of vital signs of a subject is enabled while the subject may be quasi-static, which may allow detecting of vital signs in a real-life situation.

According to an embodiment, the system may further comprise a transmitter for transmitting a radio frequency signal towards the subject. The system may thus comprise both the transmitter and the receiver for performing radar-based detection of vital signs of a subject.

According to a third aspect, there is provided a computer program product comprising a computer-readable medium with computer-readable instructions such that when executed on a processor the computer program will cause the processor to receive a baseband signal based on a reflected radio frequency signal from a subject and a transmitted signal, divide the baseband signal into a sequence of sliding windows, wherein each sliding window represents a time interval of the baseband signal; estimate a vital sign parameter based on the signal in at least one sliding window of the sequence of sliding windows; determine whether a vital sign parameter may be reliably estimated based on the signal in at least one sliding window of the sequence of sliding windows; on condition that the vital sign parameter may not be reliably estimated in a sliding window, determining a vital sign parameter of the sliding window based on vital sign parameters estimated in a plurality of windows representing time intervals close to the time interval of the window for which the vital sign parameter is determined.

Effects and features of this third aspect are largely analogous to those described above in connection with the first and second aspects. Embodiments mentioned in relation to the first and second aspects are largely compatible with the third aspect.

The computer program product may be provided such that a processor may be able to determine vital signs of a subject based on a signal formed when a subject may be quasi-static.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
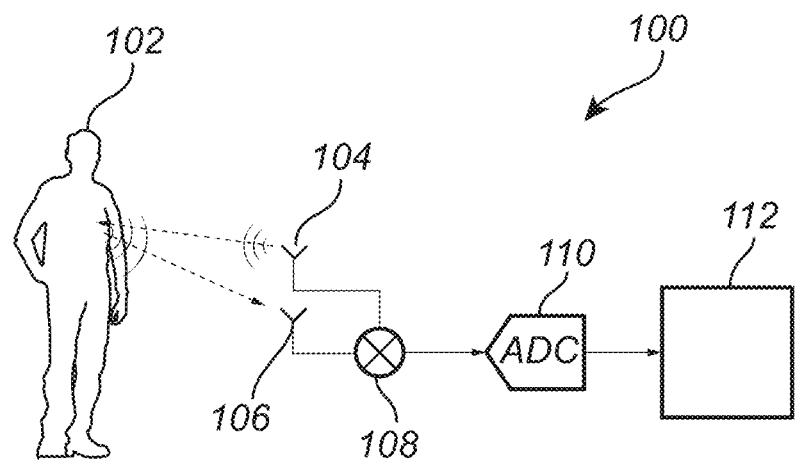
FIG. 1 is a schematic view of a device for detecting a vital sign of a subject according to an embodiment.

A method for detecting a vital sign of a subject is provided. The method uses transmitting of radio frequency signals and detecting reflected signals, wherein a baseband signal based on the reflected and transmitted signals is analyzed in order to detect vital signs. Before an embodiment of the method will be described in further detail, some general explanation of baseband signals based on vital signs and random body movements will be given.

The below explanation of effects of vital signs and random body movements is given in relation to a homodyne In-phase and Quadrature (IQ) continuous-wave (CW) radar, such that it is possible to extract a phase modulation caused by motion of the subject. A few examples of random body movements and the effect of such random body movements on detection of vital signs will be explained.

For a random chest movement, the I and Q channels may form the following signals:

$$I = DCI + B(x(t), n(t))\cos\left(\frac{4\pi}{\lambda}(x(t) + n(t))\right)$$

$$Q = DCQ + B(x(t), n(t))\sin\left(\frac{4\pi}{\lambda}(x(t) + n(t))\right)$$

where x(t) are the vital signs (forming a linear combination of respiration and heartbeat) and n(t) is a random body movement of the chest-wall, DCI and DCQ are DC offsets caused by transmitter to receiver leakage and any static reflection of the environment, B is an amplitude of the signal dependent on transmitted amplitude, reflectivity at the subject, path loss and attenuation, and λ is a wavelength of radio signal. After DC offset compensation, managing the different DC offsets DCI and DCQ, the two channels may be combined together using arctangent (AT) demodulation.

$$\varphi(t) = a\tan\left[\frac{B(x(t), n(t))\sin\left(\frac{4\pi}{\lambda}(x(t) + n(t))\right)}{B(x(t), n(t))\cos\left(\frac{4\pi}{\lambda}(x(t) + n(t))\right)}\right] == \frac{4\pi}{\lambda}(x(t) + n(t))$$

In this case the demodulated signal is a linear combination of the vital signs and the chest random movement so it is possible to extract the vital signs, as long as the random body movement n(t) is not of the same frequency as the vital signs x(t).

For a movement of one limb, the I and Q channels may form the following signals:

$$I = DCI + B(x(t))\cos\left(\frac{4\pi}{\lambda}x(t)\right) + B2(n(t))\cos\left(\frac{4\pi}{\lambda}n(t)\right)$$

$$Q = DCQ + B(x(t))\sin\left(\frac{4\pi}{\lambda}x(t)\right) + B2(n(t))\sin\left(\frac{4\pi}{\lambda}n(t)\right)$$

where x(t) are always the vital signs and n(t) is now a movement that involves only one limb generating two cosine/sine functions having amplitudes B and B2. In case of multiple limb movements, there will be additional cosine/sine functions. After DC offset compensation and AT demodulation, the resulted phase is:

$$\varphi(t) = a\tan\left[\frac{B(x(t))\sin\left(\frac{4\pi}{\lambda}x(t)\right) + B2(n(t))\sin\left(\frac{4\pi}{\lambda}n(t)\right)}{B(x(t))\cos\left(\frac{4\pi}{\lambda}x(t)\right) + B2(n(t))\cos\left(\frac{4\pi}{\lambda}n(t)\right)}\right]$$

Here using the AT demodulation, the signal will result to be a nonlinear combination of the random body movement and the vital signs. In this case, it will be almost impossible to extract the vital signs, especially when the limb movement is bigger than the vital signs motion.

For chest and limb movements, the I and Q channels may form the following signals:

$$I = DCI + B(x(t), n(t))\cos\left(\frac{4\pi}{\lambda}(x(t) + n(t))\right) + B2(n2(t))\cos\left(\frac{4\pi}{\lambda}n2(t)\right)$$

-continued $$Q = DCQ + B(x(t), n(t))\sin\left(\frac{4\pi}{\lambda}(x(t) + n(t))\right) + B2(n2(t))\sin\left(\frac{4\pi}{\lambda}n2(t)\right)$$

Here n(t) is the chest movement and n2(t) is the limb movement.

Using the AT demodulation:

$$\varphi(t) = a\tan\left[\frac{B(x(t), n(t))\sin\left(\frac{4\pi}{\lambda}(x(t) + n(t))\right) + B2(n2(t))\sin\left(\frac{4\pi}{\lambda}n2(t)\right)}{B(x(t), n(t))\cos\left(\frac{4\pi}{\lambda}(x(t) + n(t))\right) + B2(n2(t))\cos\left(\frac{4\pi}{\lambda}n2(t)\right)}\right]$$

Also in this case, there is a nonlinear combination of movements. It is clear that in real situations, the extracted signal will consist of a combination of several random body movements and the tiny vital signs signal. Finding a model on how the random movements and the vital signs are combined after the demodulation is quite complicated. It is clear that retrieving the vital signs from random body movements is not a simple task. This explains why radar-based vital signs detection is currently performed in ideal situations, namely with subjects constrained to be motionless.

With the present inventive concept, vital signs may be detected for a subject that is relatively still, such that severe constrains are not imposed on the subject. Thus, vital signs may be detected when the subject is quasi-static, such as when sitting down or lying, but possibly intermittently changing posture or otherwise randomly moving.

Referring now to FIG. 1, a device 100 for detecting a vital sign of a subject 102 will be described. The device 100 may comprise a transmitter 104 for transmitting a radio frequency signal towards the subject 102. The radio frequency signal will be reflected by the subject 102 and Doppler-shifted due to a movement of the subject 102. The movement causing a Doppler-shift may be a chest movement due to heartbeat and/or respiration of the subject 102, and information of this movement is to be extracted from the reflected signal in order to detect vital signs. However, the movement may also be a random body movement of the subject 102, which may disturb the detection of vital signs.

The device 100 further comprises a receiver 106. The receiver 106 may be configured to detect the reflected radio frequency signal from the subject 102. The detected signal and (a copy of) the transmitted signal may be mixed by a radio frequency mixer 108 in order to form a baseband signal.

The transmitter 104, receiver 106 and mixer 108 may be formed in a number of different manners by antenna(s) and associated controlling circuitry for creating and processing the radio frequency signals, as known by the person skilled in the art.

Below, description is mainly provided in relation to an IQ CW radar, which receives a reflected signal from a single subject. However, it should be realized that any radar architecture that is able to extract Doppler information may be used, such as Phase/Frequency Tracking, a radar using frequency-modulated continuous wave (FMCW), step-frequency continuous wave (SFCW), phase-modulated continuous wave (PMCW), an ultra-wideband (UWB) radar, e.g. UWB impulse radio (UWB-IR). Moreover, an UWB-based radar allows separating Doppler information of multiple targets, which may allow performing detection of vital signs at the same time for multiple subjects.

The baseband signal may be digitized in an analog-to-digital converter (ADC) 110 and may then be transmitted to a processor 112. Alternatively, the ADC may be integrated with the processor 112, which may thus be configured to receive an analog baseband signal.

The processor 112 may be configured to analyze the received baseband signal, as will be explained in further detail below. The processor 112 may be arranged remotely from the transmitter 104 and the receiver 106 and may be arranged to receive information of the digitized baseband signal through wired or wireless communication. Alternatively, the processor 112 may be integrated in a common housing with the transmitter 104 and/or the receiver 106. Furthermore, the processor 112 may be distributed on a plurality of physical units performing different parts of the operations of the processor 112.

The processor 112 may be a central processing unit (CPU). The processor 112 may thus be a general-purpose processing unit, which may be loaded with a computer program product in order to allow the processor 112 to perform the desired operations on the received baseband signal. The processor 112 may alternatively be a special-purpose circuitry for providing only specific logical operations. Thus, the processor 112 may be provided in the form of an application-specific integrated circuit (ASIC), an application-specific instruction-set processor (ASIP), a field-programmable gate array (FPGA) or a digital signal processor (DSP).

Referring now to FIGS. 2-5, processing of the baseband signal will be described in further detail. In the following, the processing of the baseband signal is mainly explained in relation to a signal that has been acquired during a period of time and is then processed. Hence, an off-line process is discussed of processing the baseband signal at a different time than the time of acquiring of the baseband signal. However, it should be realized that the processing of the baseband signal could be performed in real-time, wherein windows described below are formed "on-the-fly" as the signal is being acquired. New data may continuously be appended to data that has already been processed and allow detecting of vital signs in real-time or near real-time.

Figure 2:
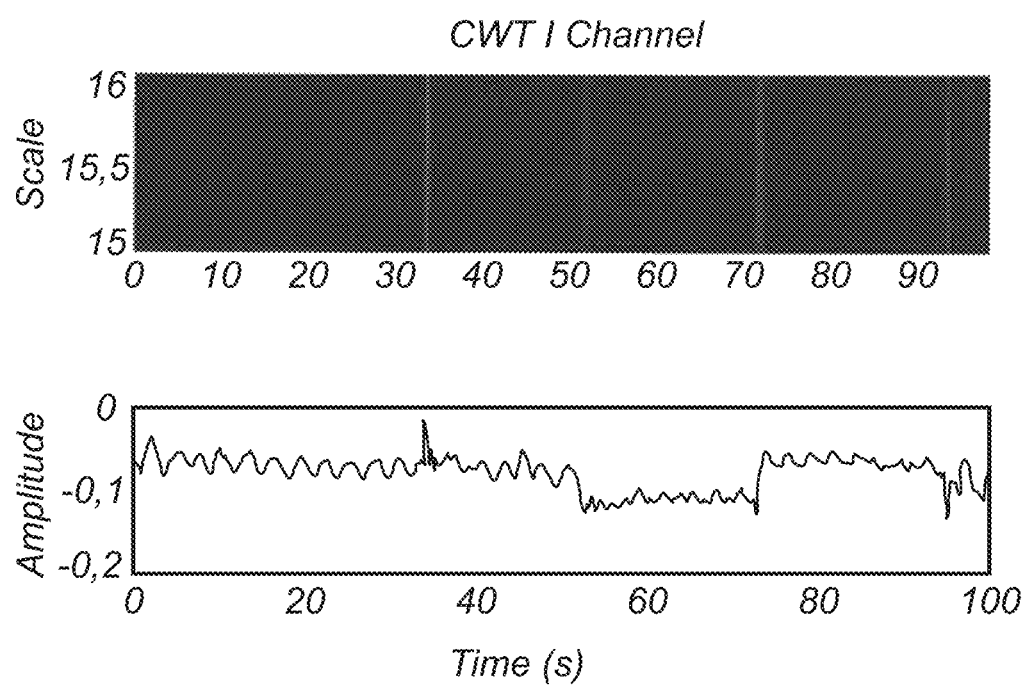
FIG. 2 is a chart illustrating an inphase channel of a baseband signal and a continuous wavelet transform of the signal for locating artefacts.

Referring to FIG. 2, the processing of the baseband signal may firstly identify presence of artefacts in the signal in order to allow artefacts to be attenuated. A transform of the baseband signal may be used in order to locate artefacts, such as continuous wavelet transform (CWT) or short-time Fourier transform (STFT).

As illustrated in FIG. 2, CWT can be used to locate the artefacts on the two IQ Channels separately, here illustrated for the I channel. For Phase/Frequency Tracking, there may only be a single channel that will be analyzed. With FMCW and SFCW signals, a single-channel receiver 106 may be used, however, the signals may still provide IQ Doppler information.

CWT is a windowing technique with variable-sized regions that allows to have different frequency and time resolutions depending on what is needed. For example, at high frequencies usually a good time resolution is necessary, but not at low frequencies where a good time resolution will only cause redundancy. With the CWT, a time-frequency representation of the signal is obtained and therefore the artefacts, that have usually also higher frequencies than the normal vital sign signals, can be clearly seen and located in time. In FIG. 2, the I Channel and its corresponding CWT is shown. The artefacts may be located in the time domain exploiting the frequency information, such that a time instance in which artefacts are present may be determined.

A threshold may be selected for locating the artefacts in the CWT representation of the baseband signal. For each sampling time, an artefact identifying algorithm may check if the CWT is higher than the threshold. If so, it is concluded that there is an artefact at the corresponding time instance.

Having identified and located artefacts, the baseband signal may be at least partially cleaned. A binary mask may be used, setting a value "1" for time instances where an artefact is present, and a value "0" if no artefact is present. The artefacts are thus located using the binary mask and it is possible to attenuate the artefacts, e.g. using a moving average filter.

Figure 3:
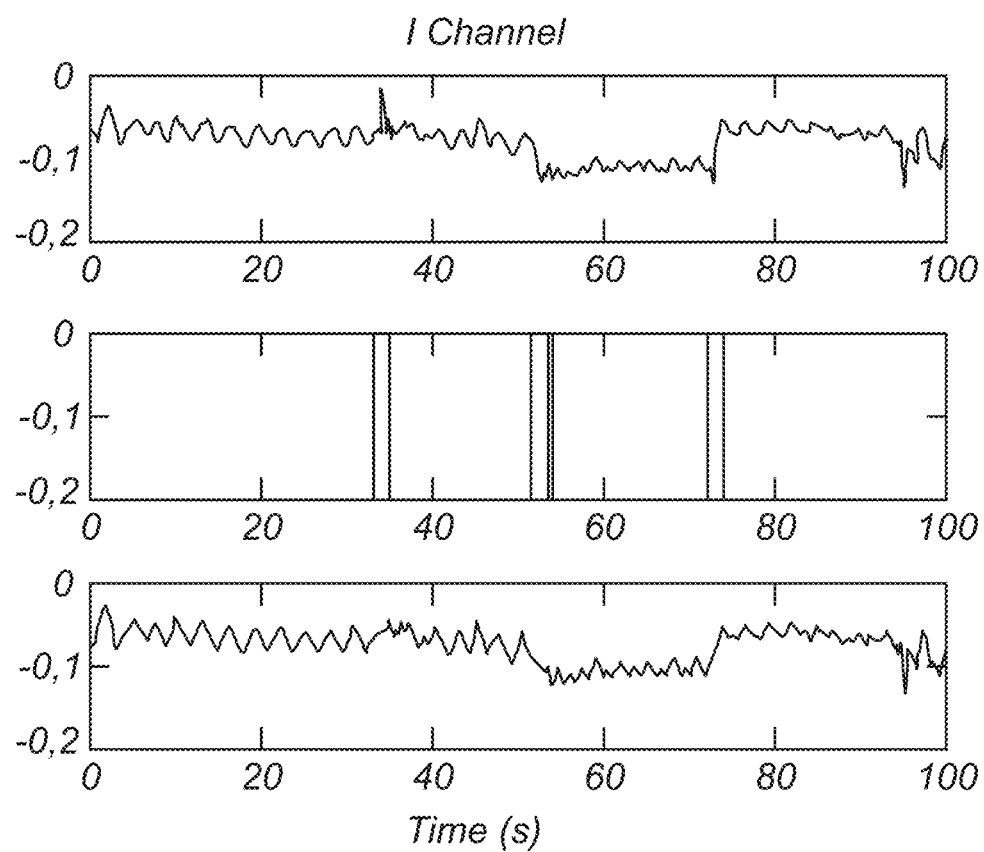
FIG. 3 is a chart illustrating the inphase channel, a binary mask and a cleaned channel.

FIG. 3 illustrates the original I channel, the mask, and the cleaned channel using a moving average filter.

Figure 4:
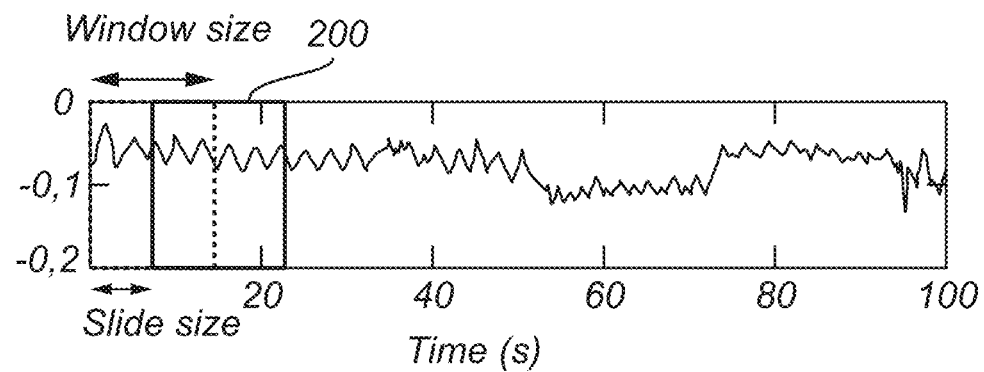
FIG. 4 is a chart illustrating sliding windows for analysis of the baseband signal.

Referring now to FIG. 4, the filtered baseband signal may be analyzed using a sliding window analysis. Thus, as illustrated in FIG. 4, the filtered baseband signal may be divided into a sequence of sliding windows 200. Each sliding window 200 may represent a time interval of the baseband signal. The sliding windows 200 may be shifted in relation to each other, such that there is a partial overlap of the time intervals of adjacent sliding windows 200.

Thus, the baseband signal is divided into a plurality of portions, represented by the sliding windows 200 and each sliding window 200 may be separately processed.

For every window, the following operations may be performed:

1. The IQ channels are combined together using a linear demodulation technique or another demodulation technique (the Phase/Frequency Tracking already produces a single demodulated signal and this operation may thus be omitted).
2. Respiration information and heartbeat information of the signal are split. Several methods can be used and will be discussed in further detail below.
3. Vital sign parameters are estimated for the signal in the window 200. Thus, a respiration rate and a heartbeat rate may be estimated. At least two different approaches may be used to estimate the rates. A Frequency Domain approach, which performs FFT processing of the signal and evaluates frequency of a highest peak in magnitude within the frequency spectrum. A Time Domain approach, which instead uses a peak detection algorithm on the time domain signals and then calculates the rates by checking the distance between two adjacent peaks. The Time domain approach may result in higher errors because of the presence of the motion artefacts and also because it may be difficult to correctly identify peaks as the vital signs signals are not perfectly sinusoidal signals.
4. Once respiration and heartbeat rates have been estimated in the current window 200, a simple check may be done to avoid high errors due to the artefacts. Heartbeat rate and respiration rate do not change suddenly. Therefore, for both respiration and heartbeat, if the estimated rate in the current window 200 differs too much (for example 6 Beats per Minute (BPM)) from the estimated rate in the previous window, the estimated rate may be replaced by the average of some of the previous estimated rates (for example the previous 5 rates). It is also possible to consider multiple previous windows, when determining whether the estimated rate for the current window 200 is reliable. This ensures that the artefacts present in the signals will not cause high errors.
5. Move to the next window 200 and repeat from point 1 above.

As indicated above, the processing of a sliding window 200 may be used for determining whether a vital sign parameter may be reliably estimated based on the signal in a sliding window 200, by means of determining whether an estimated rate in the current window 200 differs too much from the estimated rate in the previous window. However, the determining that a vital sign parameter may not be reliably estimated based on the signal in the sliding window 200 could alternatively be based on determining that a signal quality in the sliding window 200 is too low, e.g. based on analysis of the CWT representation or further processing of the signal in the current sliding window 200. Hence, if such determination may be made, the signal in the sliding window 200 (defective sliding window) need not be processed in order to try to estimate a rate based on that defective sliding window 200. Rather, the estimated rate for the defective sliding window 200 may be determined as the average of some of the previous estimated rates without making an effort to estimate the rate from the defective sliding window 200.

A window size may need to be intelligently selected. Usually in a sliding window approach, longer windows are preferred because it means that the frequency resolution will be better and so the rates can be estimated more precisely. However, in this case, longer windows mean also that more windows will contain artefacts and the estimated rates will therefore not be precise. Thus, the window size should not be too long and not be too short.

Figure 5:
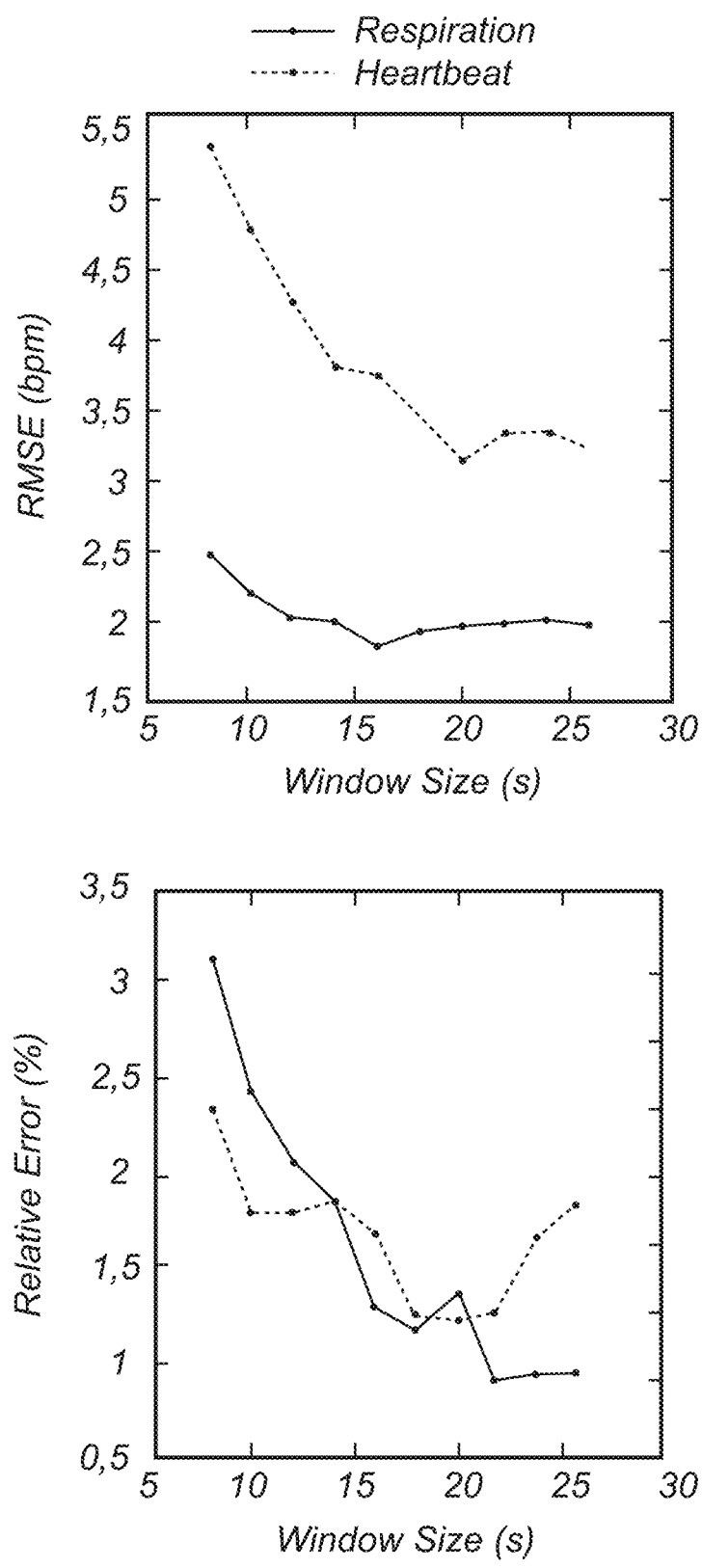
FIG. 5 shows charts of results of estimated rates of vital signs based on window sizes of the sliding windows.

In FIG. 5, results of a test of how errors change by varying the window size from 8 seconds to 26 seconds is illustrated. To understand how precisely the rates can be estimated the radar-determined respiratory rate is compared to a Respiration Belt Signal and the radar-determined heartbeat rate is compared to a photoplethysmogram (PPG). For this data set, the better window size both for respiratory rate and for heartbeat rate seems to be 18 seconds. A window size in a range of 10-25 seconds may be providing acceptable results. However, the window size can also be subject-dependent, so the window size may need to be adjusted for different subjects.

For instance, an initial analysis of the baseband signal may first be performed in order to determine a window size to be used. The initial analysis may include using a first default value of the window size and determining whether it would be beneficial to change the window size setting.

As mentioned above, respiration information and heartbeat information of the signal may be split which may facilitate accurately determining the respiratory rate and the heartbeat rate.

Since respiration and heartbeat are at different frequencies one of the simplest methods to split them is to use digital filters. Finite impulse response (FIR) filters are usually preferred because FIR filters may be designed to have a phase response that is a linear function of frequency and hence may allow to avoid distortions. However, for splitting respiration information from heartbeat information, usually a transition band between respiration information and heartbeat information has a width of around 0.4 Hz to 0.8 Hz, but the transition band may be wider, such as up to 1.2 Hz, e.g. depending on an age of the subject, considering also respiration harmonics, so a steep band transition is necessary. Respiration information may also include second, third, and even fourth order harmonics, as the mechanical movement due to respiration is not perfectly sinusoidal. The higher order harmonics may thus be in same or almost same frequency range as the hearbeat rate, which may imply that the transition band may even be smaller than 0.4 Hz.

This means that high order FIR filters should be used to reach a good separation and so distortions of the time domain signals may occur because of Gibbs phenomena. Therefore, to avoid distortions a smooth transition band has to be used. This means that it is most likely that the heartbeat signal will not be completely retrieved because respiration and respiration harmonics will not be attenuated enough in the heartbeat signal. Thus, more advanced signal processing techniques may be required.

Blind Source Separation (BSS) such as Independent Component Analysis (ICA) has been used to split two signals using two different CW radars working at different frequencies to avoid interference. ICA has also been used with multiple receivers to split respiration and heartbeat from two persons. Hence, ICA could be used for splitting the baseband signal into heartbeat information and respiration information.

However, the standard ICA method can be used to separate independent signals only if a number of observations is greater than or equal to a number of sources. This means that with a single radar, the ICA method cannot separate heartbeat from respiration (one observation, two sources).

Here, it is proposed that Wavelet Independent Component Analysis (WICA) is used in order to split the baseband signal into a respiration information carrying signal and a heartbeat information carrying signal. This method is classified as undetermined ICA because it allows retrieving the original sources with just one observation.

The WICA method is a combination between Wavelet Decomposition and ICA. Wavelet Decomposition is a method that decomposes the signal into several Components with disjoint spectra. The decomposition is quite simple. The entire signal is split into two signals using a Low Pass filter and an High Pass filter. The part that contains the low frequencies is called Approximation and the part that contains the high frequency information instead is called Detail. The decomposition then can be continued decomposing the Approximation in its own approximation and detail and so on. The decomposition is then formed by all the details and the last approximation. These components may be used as input for the ICA method, which may then separately retrieve the respiration information and the heartbeat information.

According to an alternative embodiment, it is proposed that Ensemble Empirical Mode Decomposition Independent Component Analysis (EEMDICA) is used in order to split the baseband signal into a respiration information carrying signal and a heartbeat information carrying signal. This method is also classified as undetermined ICA. Empirical Mode Decomposition (EMD) is a data-driven algorithm that decomposes an original signal into a set of oscillatory modes called Intrinsic Mode Functions (IMFs). However, the EMD algorithm is sensitive to noise. Ensemble EMD (EEMD) is a noise-assisted version of the algorithm that guarantees robustness. An ensemble of trials is applied to the signal where an independent identically distributed white noise is added. The white noise populates the entire spectrum and EMD behaves as a dyadic filter. After the EEMD is performed the ICA can be applied on the entire set of IMFs.

Figure 6:
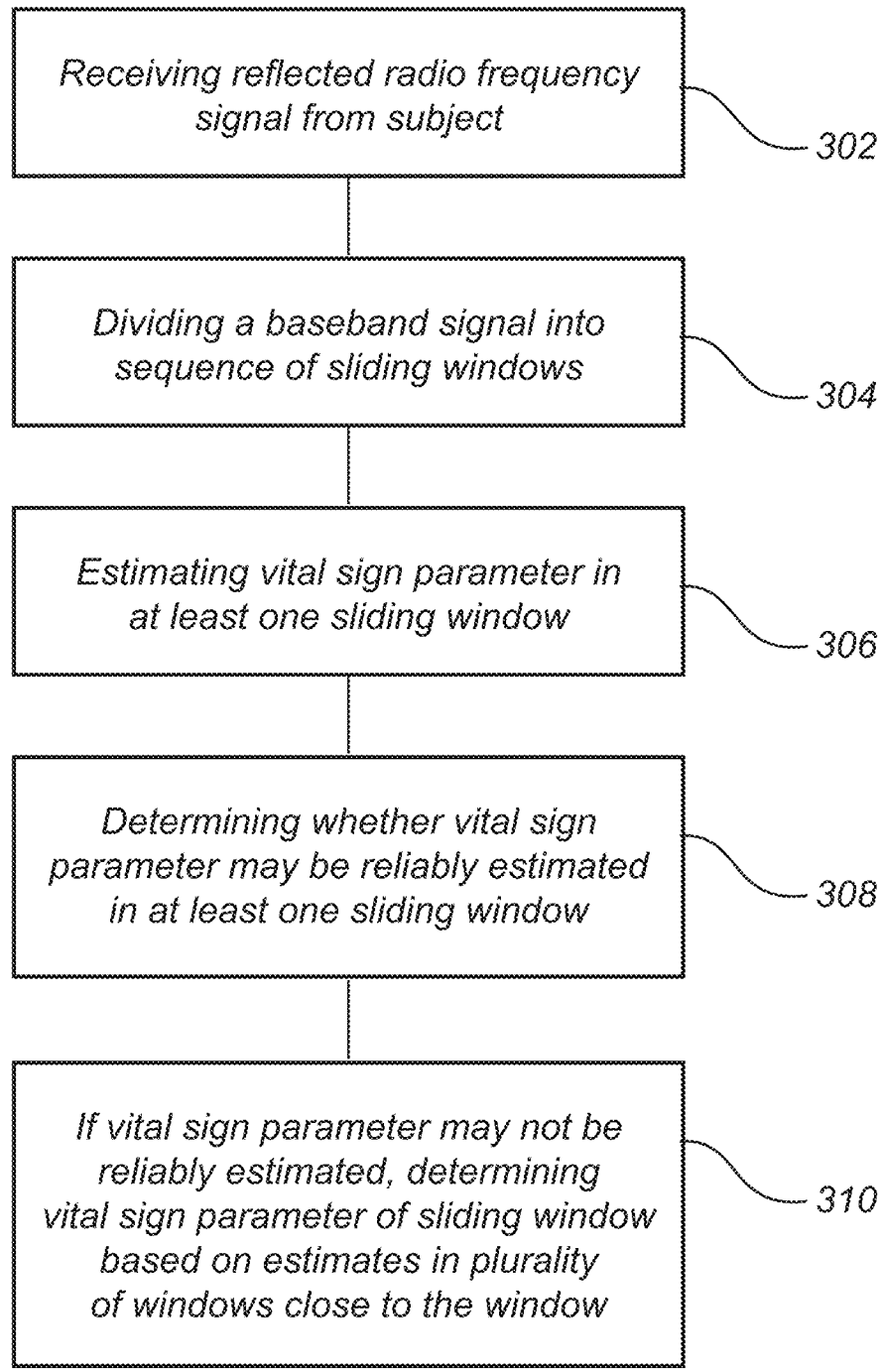
FIG. 6 is a flow chart of a method according to an embodiment.

Referring now to FIG. 6, a method for detecting a vital sign of a subject 102, comprising at least one of a heart rate and a respiratory rate of the subject 102, according to an embodiment will be briefly summarized.

The method comprises receiving 302 a reflected radio frequency signal from the subject 102, the reflected signal being based on a transmitted signal, which is Doppler-shifted due to mechanical movements corresponding to at least one of the heart rate and the respiratory rate to form the reflected signal.

The method further comprises dividing 304 a baseband signal based on the received signal and the transmitted signal into a sequence of sliding windows 200, wherein each sliding window 200 represents a time interval of the baseband signal.

The method further comprises estimating 306 a vital sign parameter based on the signal in at least one sliding window of the sequence of sliding windows 200. The estimation of the vital sign parameter may be performed for each sliding window 200. However, the signal may first be processed in order to find artefacts and such processing may also be used to determine defective sliding windows for which signal quality is insufficient for reliably determining a vital sign parameter, even after cleaning of artefacts from the signal. Thus, estimation of the vital sign parameter need not be performed for such defective sliding windows.

The method may further comprise determining 308 whether a vital sign parameter may be reliably estimated based on the signal in at least one sliding window 200 of the sequence of sliding windows. The determining whether a vital sign parameter may be reliably estimated may be performed in advance of estimating of vital sign parameters for sliding windows. However, the determining whether a vital sign parameter may be reliably estimated may alternatively be based on the estimation of the vital sign parameter for the sliding window and assessing whether the estimation is plausible. The assessment whether the estimation is plausible may comprise comparing the estimated rate to physiologically plausible rates and/or comparing the estimated rate to estimated rate(s) for one or more adjacent sliding windows 200. If a difference between the estimated rate for a current sliding window and the estimated rate(s) of the one or more adjacent sliding windows is larger than a threshold, the current sliding window may be considered to not enable reliably estimating the vital sign parameter.

On condition that the vital sign parameter may not be reliably estimated in a sliding window, the method further comprises determining 310 a vital sign parameter of the sliding window based on vital sign parameters estimated in a plurality of windows representing time intervals close to the time interval of the window for which the vital sign parameter is determined. Thus, an estimated rate may still be determined for the sliding window, allowing the vital sign parameter to be determined even for defective sliding windows.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For example, the sliding windows 200 are described above as being arranged with a partial overlap between adjacent sliding windows 200. It should be realized that the sliding windows 200 may instead be arranged consecutively, such that start of a time interval of a sliding window may coincide with end of the time interval of the previous sliding window.

The invention claimed is:

1. A method for detecting a vital sign of a subject, wherein the vital sign comprises at least one of a heart rate or a respiratory rate of the subject, said method comprising:
   receiving a reflected radio frequency signal from the subject, the reflected radio frequency signal being based on a transmitted signal, which is Doppler-shifted due to mechanical movements corresponding to at least one of the heart rate or the respiratory rate to form the reflected radio frequency signal;
   dividing a baseband signal based on the received reflected radio frequency signal and the transmitted signal into a sequence of sliding windows, wherein each sliding window represents a time interval of the baseband signal;
   estimating a vital sign parameter based on the baseband signal in at least one sliding window of the sequence of sliding windows;
   determining whether the vital sign parameter may be reliably estimated based on the baseband signal in the at least one sliding window of the sequence of sliding windows; and
   on condition that the vital sign parameter may not be reliably estimated in the at least one sliding window, determining the vital sign parameter of the at least one sliding window based on vital sign parameters estimated in a plurality of sliding windows representing time intervals close to the time interval of the at least one sliding window for which the vital sign parameter is determined.

2. The method according to claim 1, wherein two adjacent sliding windows in the sequence of sliding windows represent partially overlapping time intervals.

3. The method according to claim 1, wherein said determining whether the vital sign parameter may be reliably estimated based on the baseband signal in at least one sliding window of the sequence of sliding windows comprises comparing the estimated vital sign parameters of pairs of adjacent windows and determining whether a difference in the estimated vital sign parameters is above a threshold.

4. The method according to claim 1, further comprising at least partially cleaning the baseband signal to attenuate influence of artefacts.

5. The method according to claim 4, wherein at least partially cleaning the baseband signal comprises determining time instances in the baseband signal in which an artefact is present.

6. The method according to claim 5, wherein determining time instances in the baseband signal in which an artefact is present comprises analyzing the baseband signal to determine the time instances in which undesired high frequency components are present.

7. The method according to claim 5, wherein at least partially cleaning the baseband signal further comprises applying a moving average filter to the baseband signal in the determined time instances in which an artefact is present.

8. The method according to claim 1, wherein estimating the vital sign parameter comprises converting the baseband signal in the at least one sliding window to frequency domain and determining an estimated heart rate or respiratory rate based on a frequency of a peak in a frequency domain spectrum.

9. The method according to claim 8, wherein determining the estimated heart rate or an estimated respiratory rate comprises ignoring rates which are outside a range of physiologically plausible rates.

10. The method according to claim 1, wherein estimating he vital sign parameter comprises detecting peaks in the baseband signal in the at least one sliding window and determining an estimated heart rate or an estimated respiratory rate based on distance between adjacent peaks.

11. The method according to claim 1, further comprising receiving a window size setting and using the window size setting for defining a length of the time interval of each sliding window when dividing the baseband signal into the sequence of sliding windows.

12. The method according to claim 1, further comprising splitting the baseband signal into a respiration information carrying signal and a heartbeat information carrying signal, performing estimation of the respiratory rate based on the respiration information carrying signal, and performing estimation of the heart rate based on the heartbeat information carrying signal.

13. The method according to claim 12, wherein said splitting of the baseband signal comprises performing wavelet decomposition of the baseband signal and using components produced by the wavelet decomposition as input to an independent component analysis for splitting the baseband signal.

14. The method according to claim 12, wherein said splitting of the baseband signal comprises decomposing the baseband signal into intrinsic mode functions using an ensemble empirical mode decomposition (EEMD) algorithm and using the intrinsic mode functions as input to an independent component analysis for splitting the baseband signal.

15. A device for detecting a vital sign of a subject, wherein the vital sign comprises at least one of a heart rate or a respiratory rate of the subject, said device comprising:
   a receiver, configured to detect a reflected radio frequency signal from the subject, the reflected radio frequency signal being based on a transmitted signal, which is Doppler-shifted due to mechanical movements corresponding to at least one of the heart rate or the respiratory rate to form the reflected radio frequency signal; and
   a processor, which is configured to receive a baseband signal based on the detected reflected radio frequency signal from the receiver and the transmitted signal and which is further configured to:
     divide the baseband signal into a sequence of sliding windows, wherein each sliding window represents a time interval of the baseband signal,
     estimate a vital sign parameter based on the baseband signal in at least one sliding window of the sequence of sliding windows,
     determine whether the vital sign parameter may be reliably estimated based on the baseband signal in the at least one sliding window of the sequence of sliding windows, and
     on condition that the vital sign parameter may not be reliably estimated in the at least one sliding window, determine the vital sign parameter of the at least one sliding window based on vital sign parameters estimated in a plurality of sliding windows representing time intervals close to the time interval of the at least one sliding window for which the vital sign parameter is determined.

* * * * *